US00PP37753P2

(12) United States Plant Patent
Bouchet

(10) Patent No.: US PP37,753 P2
(45) Date of Patent: Oct. 13, 2026

(54) CHERRY TREE NAMED 'SWILAM'

(50) Latin Name: ***Prunus avium* (L.) L.**
Varietal Denomination: SWILAM

(71) Applicant: Agro Selections Fruits S.A.S., Elne Cedex (FR)

(72) Inventor: Christophe Bouchet, Elne Cedex (FR)

(73) Assignee: AGRO SELECTIONS FRUITS S.A.S., Elne Cedex (FR)

( * ) Notice: Subject to any disclaimer, the term of this patent is extended or adjusted under 35 U.S.C. 154(b) by 0 days.

(21) Appl. No.: 18/831,904

(22) Filed: Nov. 5, 2025

(30) Foreign Application Priority Data

Nov. 28, 2024 (QZ) ..... PBR 2024/2835

(51) Int. Cl.
*A01H 5/08* (2018.01)

(52) U.S. Cl.
USPC ..... Plt./181

(58) Field of Classification Search
USPC ..... Plt./181
CPC ..... A01H 6/7445; A01H 5/08
See application file for complete search history.

*Primary Examiner* — Keith O. Robinson
(74) *Attorney, Agent, or Firm* — Birch, Stewart, Kolasch & Birch, LLP

(57) ABSTRACT

A new and distinct variety of cherry tree denominated 'SWILAM' has fruits that ripen medium in the season, with large size and dark red skin, firm, and with a good flavor and eating quality; the fruit is further characterized by its good handling and storage qualities.

4 Drawing Sheets

Latin name of the genus and species of the plant claimed: *Prunus avium* (L.) L.

Variety denomination: 'SWILAM'.

This application claims priority of Community plant variety right No. 2024/2835 filed on Nov. 28, 2024 which is hereby incorporated by reference in its entirety.

The new variety named 'SWILAM' is also known as 'EL.02.15.42.09CE' or 'ASF0907TH'. Indeed, before giving a name to a new and distinct variety of fruit tree, a provisional reference is assigned, considering the references of a tree in orchard. This provisional reference is constituted firstly with the first letters of the location where the variety has been selected, then the number of the parcel on which the tree has grown, then the number of the line, the tree number and usually the year of selection. Then before being named 'SWILAM', the provisional reference of this cherry tree variety was EL.02.15.42.09CE, corresponding to the tree 42 located in line 15 of the parcel 02, and selected during the year 2009, and selected in the location named "ELNE". The letters "CE" are related to the first letters of the type of tree in French (CE for "CErise", that means "cherry"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'SWILAM', the clone reference was 'ASF0907TH', which can also be more simply referred to as 'ASF0907'.

BACKGROUND OF THE NEW VARIETY

Field of the Invention

In the field of plant genetics, we conduct an extensive and continuing plant-breeding program including the organization and reproduction of orchard trees, among which peaches, nectarines, apricots, apples, and cherries are exemplary. It was against this background of our activities that the present variety of cherry tree was originated and reproduced by us in our experimental orchard located near Elne, Pyrénées Orientales, France.

ORIGIN OF THE VARIETY

The present invention relates to a new a distinct variety of cherry tree *Prunus avium* L. which has been given the variety denomination 'SWILAM'. This tree produces fruits with a long shelf life without alteration both on the trees after growth completion and after harvesting, very good eating quality with a medium red colored flesh, and for fresh market during June in the Pyrénées Orientales department, France.

Contrast is made to 'BICOLAM' cherry tree (U.S. Plant Pat. No. 31,686), 'FIRELAM' cherry tree (U.S. Plant Pat. No. 25,564), and 'BIGALISE' (not patented) cherry tree for reliable description. 'SWILAM' is a promising candidate for commercial success in that it produces very attractive fruits having a long shelf life.

The present new variety of cherry tree (*Prunus avium* L.) was developed by us in our experimental orchard located in France. 'SWILAM' cherry tree originated in a cultivated area of the South of France, in the Pyrénées-Orientales department where it was also tested. This zone also called Roussillon is subject to a Mediterranean climate. The winter is generally sweet that is to say the total amount of cold hours lower than 7° C. (Celsius) varies from 600 hours to 1200 hours. The summer is hot and dry, that is to say the total amount of sunshine hours is an average of 2400 hours to 2800 hours per year. The prevailing wind is called "Tramontane": it dries the air and clear the sky from clouds, but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen, and the summer is dry with a few thunderstorms.

The 'SWILAM' variety resulted from an open pollination of the cherry tree variety named 'RUBILAM' (U.S. Plant Pat. No. 23,798) which was used as the seed parent. Thus, the pollen parent is unknown.

The 'SWILAM' variety was obtained by hybridizing and propagated by grafting on a 'Maxma14' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

Compared to its seed parent, a red cherry tree named 'RUBILAM' (U.S. Plant Pat. No. 23,798) as set forth above, the new 'SWILAM' variety flowers 10 days earlier and ripens 4 days earlier than the 'RUBILAM' variety. In addition, the fruits of the new 'SWILAM' variety are generally larger and kidney-shaped (or reniform), while the fruits of the 'RUBILAM' variety are more heart-shaped.

Compared to the cherry tree named 'BICOLAM' (U.S. Plant Pat. No. 31,686), the new variety 'SWILAM' shows a later maturity period. Indeed, the first fruits of the new variety 'SWILAM' ripen approximately five days later than the first fruits of the similar variety 'BICOLAM'.

In addition, compared to the fruits produced by the similar cherry variety named 'BICOLAM', the fruits of the new variety 'SWILAM' are considered to be firmer. Indeed, the firmness of 'BICOLAM' fruits is between 61 and 67 on the Duforel scale, while 'SWILAM' fruit is between 65 and 74 on the same scale.

Furthermore, the acidity of 'SWILAM' fruits is higher, approximately 11,12 while the acidity of the similar 'BICOLAM' variety is approximately 4,5. The fruits of the new variety 'SWILAM' can also be considered as more sugary than those of the 'BICOLAM' variety. Indeed, the degrees brix of the 'SWILAM' fruits is higher, typically around 18.8 on average, than the degrees Brix of the 'BICOLAM' fruits, which is approximately 16.9. The percentage of acidity in 'SWILAM' variety is therefore quite low compared to traditional varieties. The result is a sweeter cherry, as the Brix level compensates for the acidity level.

Compared to the 'FIRELAM' (U.S. Plant Pat. No. 25,564) fruits, the fruits of the 'SWILAM' variety are also considered to be firmer. Indeed, the firmness of 'FIRELAM' fruits is between 44 and 58 on the Duforel scale.

Compared to the cherry tree named 'BIGALISE' (non patented), the new variety 'SWILAM' shows an earlier maturity date. Indeed, the first fruits of the new variety 'SWILAM' ripen approximately five days earlier than the first fruits of the similar variety 'BIGALISE'.

In addition, compared to the fruits produced by the similar cherry variety named 'BIGALISE', the fruits of the new variety 'SWILAM' are considered to be firmer. Indeed, the firmness of 'BIGALISE' fruits is between 58 and 65 on the Duforel scale, while 'SWILAM' fruit is between 65 and 74 on the same scale firmness.

Furthermore, the fruits of the new variety 'SWILAM' can also be considered as more sugary than those of the 'BIGALISE' variety. Indeed, the degrees brix of the 'SWILAM' fruits is higher, typically around 19.4, than the degrees Brix of the 'BIGALISE' fruits, which is approximately 16.3.

In addition, the color of the fruit skin of the new variety 'SWILAM' is considered dark red, while the fruit skin of the similar variety 'BIGALISE' is considered red.

SUMMARY OF THE NEW VARIETY

The new variety 'SWILAM' produces fruits of large size, firm, with a semi-sweet flavor, low acidity, and a dark red color of skin. The blooming period is considered early for the variety, generally at the end of March. The maturity period is considered medium, and generally begins at the end of May or early in June, in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
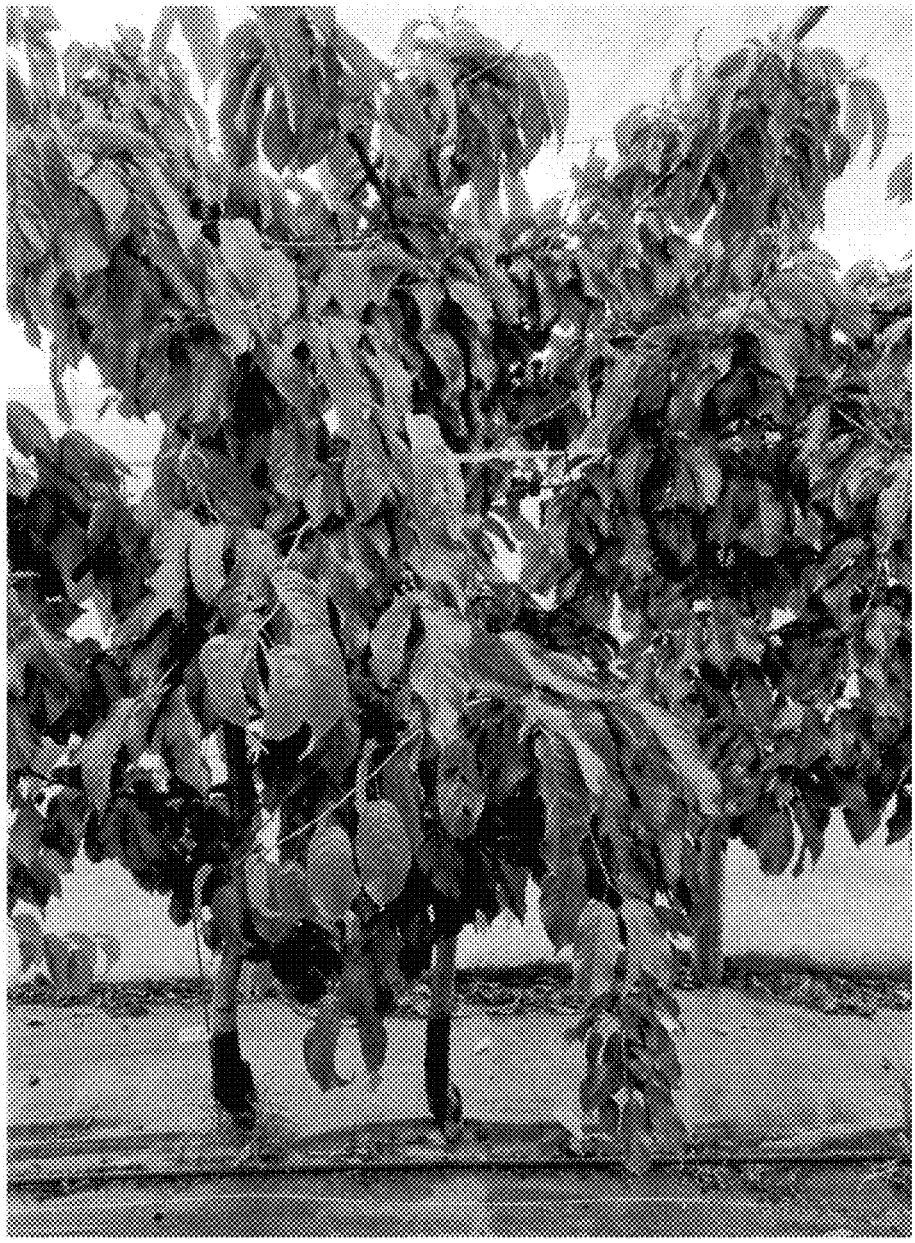
FIG. 1 is a color photograph which shows a view of a tree of the new variety in orchard at ripening time.
Figure 2:
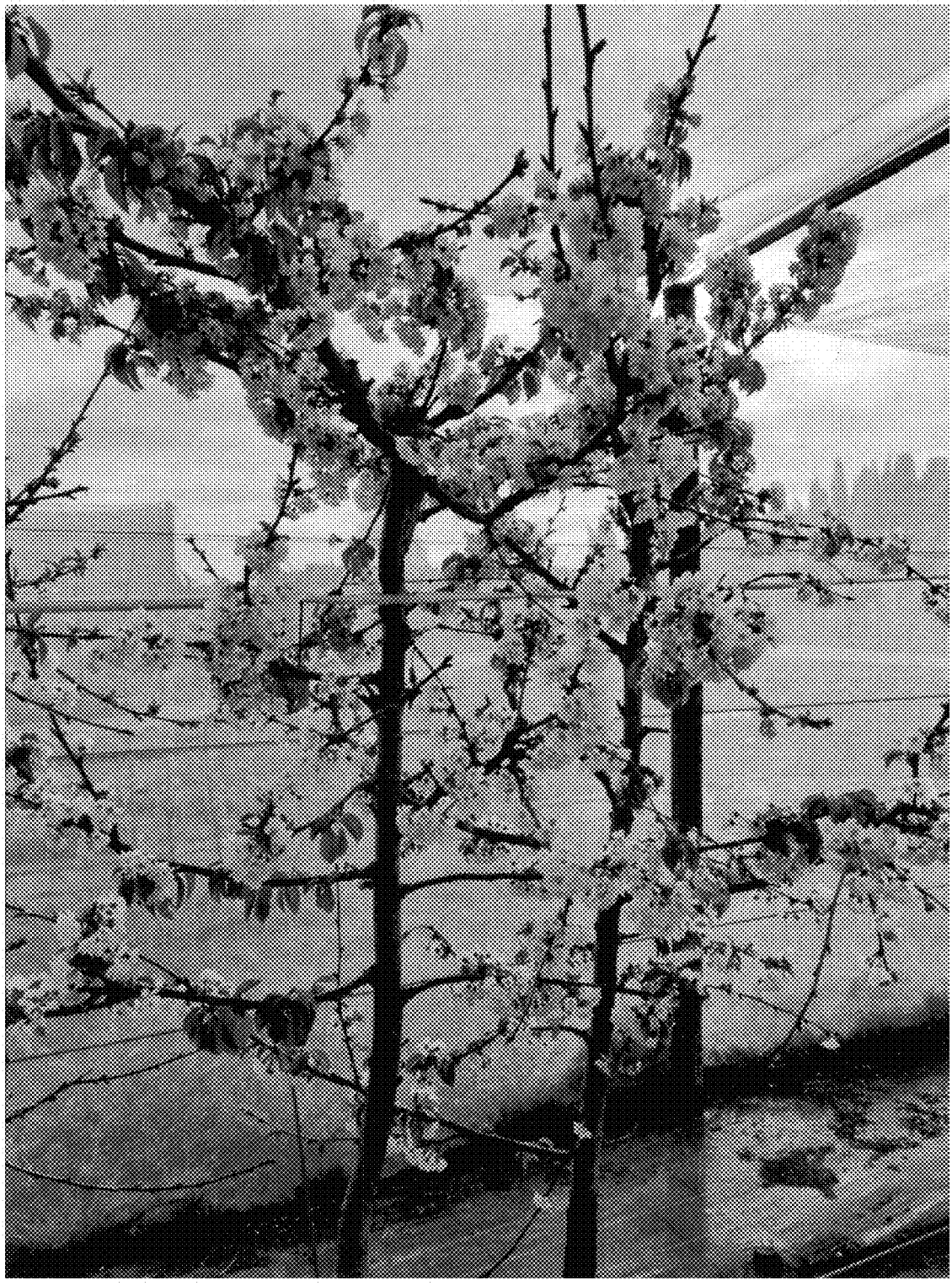
FIG. 2 is a color photograph which shows a view of a tree of the new variety in orchard at blossoming time.

The enclosed photographs show plants in their fifth growing season, except for flowers, that have been observed in their sixth growing season.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of cherry tree, its flowers, foliage and fruit, as based on observations of specimens grown near Elne, South of France, with color in accordance with The R.H.S. (Royal Horticultural Society) Colour Chart (Fourth Edition) provided by The Royal Horticultural Society of Great Britain.

The trees, flowers and fruits may vary in slight detail due to variations in soil type, cultural practices and climatic conditions.

The main characteristics of this new variety of semi-sweet cherry are a big fruit size with dark red skin. The color of fruit flesh is red to blood red. The fruit is firm. The beginning of flowering is early and the ripening period is also considered medium.

DETAILED DESCRIPTION

Referring more specifically to the pomological details of this new and distinct variety of cherry tree, the following has been observed on trees on their ninth growing season (eighth year of production) for trees, trunks, and stones and on trees on their eighth growing season (seventh year of production) for leaves, flowers and fruits, under the ecological conditions prevailing at the orchards located near the town of Elne, Pyrénées-Orientales department, France.

All observations have been done on rootstock cultivar. The rootstock was a 'MAXMA14' tree. All major color code designations are by reference to The R.H.S. (Royal Horticultural Society) Colour Chart 2001 (Fourth Edition) provided by The Royal Horticultural Society of Great Britain.

Tree:

Generally: The first year the cherry tree is generally cut at 2.50 meters height. The length in one year for each lateral shoot varies from 0.60 meters to 0.80 meters. We are cutting the cherry trees during the second year to a height of 2.50 meters. The form of the cheery trees is cylindrical and the diameter is limited to 1 meter.

*Size*.—Medium to high as compared to other commercial sweet cherry cultivars. The tree size the first year was approximately 2.50 meters. The tree was pruned during each following dormant season to a height of approximately 2.50 meters. Current season's shoots growth could reach 0.60 to 0.80 meters. So the tree size from the second year (second and next years) reached a final height of 3.10 to 3.30 meters with current seasons shoots length comprised. The mature branches have been pruned to a length of 30.0 centimeters in order to place nets on the trees.

*Spread*.—Approximately 2.0 meters with a cylindrical shape. The whole orchard was oriented to a central leader organization, with tree lines spaced of 4.0 meters and trees spaced of 1 meter in a same tree line.

*Vigor*.—Medium, tree growth reaching 0.60 to 0.80 meters the first growing season.

*Productivity*.—Very good productivity, every year. The new variety produces adequate fruit set annually on a regular basis. The number of the fruit set varies with the prevailing climatic conditions and cultivar practices employed during the bloom period and is therefore not distinctive of the present variety.

*Bearer*.—Very regular and quantitative. The extinction of the clusters of May improves the size and firmness of the fruit.

*Form*.—Semi-spread to spread.

*Hardiness*.—Medium in all stone fruit growing areas of France and especially where the chilling requirement is between 350 and 1200 hours. No injury with temperatures as low as-12° C. in winter. Good resistance to late frosts. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017 and 1017 hours in 2017-2018, 844 hours in 2018-2019, 721 hours in 2019-2020, 862 hours in 2020-2021, 817 hours in 2021-2022, 949 hours in 2022-2023, 690 hours in 2023-2024, and 723 hours in 2024-2025, showed a good behavior of the tree in all cases.

Trunk:

*Size*.—Medium. Approximately 72.0 to 78.0 millimeters above 20.0 centimeters from ground, on $9^{th}$ growing season.

*Bark texture*.—Rough with reliefs due to the lenticels.

*Lenticels*.—High number of lenticels. The number of lenticels reaches approximately 2 lenticels per 1 $cm^2$. At the $9^{th}$ growing season, lenticels are 3.0 to 3.5 millimeters in height and 1.0 to 1.5 millimeters in width.

*Lenticels color*.—Color of lenticels is brown to orange (RHS GREYED ORANGE 164 A or RHS GREYED ORANGE 164 B).

*Bark color*.—Grey (RHS GREY 201 C or RHS GREY 201 D).

Mature branches:

*Size*.—Medium for the branches at the $9^{th}$ growing season.

*Diameter*.—Average diameter of 17 to 22 millimeters.

*Crotch angles*.—The crotch angles are generally between 75 to 90 degrees from the vertical axis. This particular characteristic is not considered distinctive of the variety, however.

*Internode*.—Between 45 and 55 millimeters.

*Color*.—Mature branches show a brown color (RHS BROWN N200 A).

*Surface texture*.—Smooth with medium lenticels, with a stretched shape. Wood that is several years old has furrowed appearance.

*Lenticels*.—The number of lenticels reaches 2 lenticels per 1 $cm^2$. The lenticels are 2.0 to 2.5 millimeters in height and approximately 0.5 to 1.0 millimeter in width.

*Lenticel color*.—The color of lenticels is considered orange (RHS GREYED ORANGE 164 A or RHS GREYED ORANGE 164 B).

Current season shoots and two years old branches:

*Size*.—Medium for the new growth, between 60.0 and 80.0 centimeters.

*Diameter*.—Considered medium. Average diameter of about 3.0 to 3.5 millimeters for current season shoots and between 6.5 and 8.0 millimeters for branches in their $2^{nd}$ growing season.

*Surface texture*.—Smooth with small lenticels on current season shoots, and medium lenticels on branches in their $2^{nd}$ growing season.

*Lenticels on current season shoots*.—The lenticels on current season shoots are considered small, round, with a diameter comprised between 0.5 and 1.0 millimeter. The number of lenticels reaches 1 or 2 lenticel(s) per $cm^2$.

*Lenticels on branches in their 2nd growing season.*—The lenticels on two years old branches are considered medium in size, with a stretched shape. The number of lenticels reaches 2 lenticels per 1 $cm^2$. The lenticels are 2.0 to 2.5 millimeters in height and approximately 0.5 to 1.0 millimeter in width.

*Lenticel color.*—The color of lenticels is considered orange (RHS GREYED ORANGE 164 A or RHS GREYED ORANGE 164 B) on current season shoots and two years old branches.

*Crotch angles.*—Primary branches are considered variable, but the crotch angles are generally 70 degrees from the vertical axis on current season shoots and on two years old branches. This particular characteristic is not considered distinctive of the variety, however.

*Internode.*—Considered medium. Generally from 32.0 millimeters to 45.0 millimeters length and 38.0 to 47.0 millimeters on two years old branches.

*Color.*—Current season shoots are considered light brown to slightly green (RHS GREY BROWN N 199 C) on their upper face and greenish (RHS YELLOW GREEN 152 B or RHS YELLOW GREEN 152 C) on their lower face.

Leaves:

*Size.*—Medium for the species. Leaf measurements have been taken from vigorous, upright, current-season growth at approximately mid-shoot. The ratio leaf length/leaf width is approximately 1.956.

*Length.*—Approximately 132.0 millimeters without leaf petiole.

*Width.*—Approximately 67.5 millimeters.

*Leaf form in cross view.*—Concave.

*Leaf form.*—Lanceolate.

*Apex.*—Attenuate.

*Leaf base.*—Round.

*Leaf margins.*—Considered dentate.

*Thickness.*—Medium.

*Uniformity.*—Leaves are generally identical.

Leaf color:

*Upper leaf surface.*—Green (RHS YELLOW GREEN 147 A).

*Lower surface.*—A lighter green than the upper leaf surface (RHS YELLOW GREEN 147 B).

*Leaf texture.*—Smooth, without pubescence (glabrous) on the upper surface. The lower surface is also smooth without pubescence.

*Leaf venation.*—Pinnately veined.

Mid-vein:

*Color.*—The mid-vein or midrib is light green (RHS YELLOW GREEN 146 B or RHS YELLOW GREEN 146 C) and the color may evolve with maturity.

*Thickness.*—Approximately 1.0 millimeter.

Lateral veins:

*Color.*—The lateral veins are considered light green (RHS YELLOW GREEN 145 A).

Leaf petioles:

*Size.*—Considered long.

*Length.*—About 31.0 to 36.0 millimeters.

*Diameter.*—About 1.0 to 1.5 millimeters.

*Texture.*—The surface of leaf petiole is smooth.

*Shape.*—Grooved.

*Color.*—Upper surface purple to brown (RHS GREYED RED 178 A). Lower surface green (RHS YELLOW GREEN 144 C).

*Ratio blade length/petiole length.*—More or less 4.0.

Leaf glands:

*Size.*—Considered medium.

*Length.*—The length of leaf glands is about 2.0 millimeters.

*Width.*—The width of leaf glands is about 1.0 millimeter.

*Number.*—Generally 2.

*Type.*—Reniform.

*Margins.*—Smooth.

*Position.*—Leaf glands are located at the base of the leaf blade.

*Color.*—On young leaves, the leaf glands are considered yellow (RHS YELLOW GREEN 145 A). The leaf gland color evolves with maturity and, on older leaves, the leaf are colored in a purple color (RHS GREYED PURPLE 183 A).

Leaf stipules:

*Generally.*—No leaf stipules were observed.

Flowers:

Flower buds:

*Generally.*—At pre-floral stage of development, the floral bunches are make up with 3 to 5 floral buds having a round shape with a round tip. Their form is evolving until blooming, with variables dimensions. Then, just before blooming, floral buds have a width of about 6.0 to 7.0 millimeters and are approximately 12.0 to 14.0 millimeters long. The distribution of the flower buds is considered homogenous on the trees.

*Color.*—This characteristic is dependent upon the proximity to bloom. At pre-floral stage of development, the bottom of the flower's buds, or calyx, or flower receptacle, formed by sepals, is green or light green color at the inner surface (RHS YELLOW GREEN 151 A or RHS YELLOW GREEN 151 B). The outer surface of the calyx is considered green (RHS YELLOW GREEN 145 A). Above the calyx, the corolla, formed by petals, is generally pure white (RHS WHITE NN155 C) on both upper and lower surfaces.

*Hardiness.*—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom.*—Generally late March for the beginning of blooming. Last four blooms took place respectively from March 23rd to Mar. 30, 2021, then from March 21st to Mar. 28, 2022, then from March 23rd to Mar. 30, 2023, and then from March 25th to Apr. 1, 2024, then from March 29th to Apr. 4, 2025.

*Blooming time.*—Considered early relative comparison to other commercial cherry cultivars grown in the Pyrénées-Orientales department, France. The date of full bloom is observed at the middle of the blooming period. The date of bloom varies slightly with climatic conditions and cultural practices.

*Blooming period.*—The flowering period lasts 8 days. This characteristic varies slightly with the prevailing climatic conditions.

*Flower type.*—The variety is considered to have a showy type of flowers (rosette).

*Flower size.*—Considered medium. Average diameter between 34.0 and 38.0 millimeters when totally opened.

*Bloom quantity.*—Considered abundant or very abundant, approximately 80 to 85 flowers per meter.

*Flower bud frequency.*—Generally 3 to 5 flower buds appear per node.

Petal:

*Size.*—Considered medium to large for the species.

*Length.*—Generally between 18.0 and 20.0 millimeters.

*Width.*—Generally between 18.0 and 19.0 millimeters.

*Petal form.*—Round.

*Petal count.*—Nearly always 5.

*Petal texture.*—Both petal surfaces have a smooth texture.

*Petal margins.*—Smooth.

*Petal apex.*—The petal apex is round shaped.

*Petal color.*—Pure white color (RHS WHITE NN155 C) on both surfaces.

*Fragrance.*—Light to moderate.

*Arrangements of petals.*—Intermediate. Slightly overlapping.

Petal claw:

*Form.*—The claw is considered to have a narrow form.

*Length.*—Approximately 1.0 millimeter.

*Width.*—Approximately 1.0 millimeter.

*Color.*—Same color as the petal's color (RHS WHITE NN155 C).

Flower pedicel:

*Length.*—Considered medium to long and having an average length of approximately 16.0 to 22.0 millimeters.

*Diameter.*—Average 1.0 millimeter.

*Color.*—Green (RHS YELLOW GREEN 145 A).

Calyx:

*Internal surface texture.*—Smooth.

*Color.*—At stage F of blooming, when the flower is open, the inner surface is of green or yellow green color (RHS YELLOW GREEN 151 C). The outer surface of the calyx is considered light green (RHS YELLOW GREEN 145 A).

Sepals:

*Surface texture.*—The outer and inner surfaces of the sepals have a smooth texture.

*Size.*—Usually considered medium to large.

*Length.*—Approximately 6.0 to 7.0 millimeters.

*Width.*—Approximately 4.0 to 5.0 millimeters.

*Shape.*—Triangular shape.

*Color.*—The color of the calyx darkens depending on the stage of development of the flower. At phenological stage F, when the flower is fully open, the upper surface is green (RHS YELLOW GREEN 145 A to RHS YELLOW GREEN 152 C) with a with a slight purple tint. The lower surface of the sepals is considered green (RHS YELLOW GREEN 145 A).

*Number of sepals.*—Generally 5, no overlapping.

*Sepal apex.*—Slightly rounded tip.

*Margins.*—Smooth.

Stamens:

*Average number of stamens per flower.*—Between 32 and 36 stamens per flower.

*Length.*—Approximately 11.0 to 14.0 millimeters, generally equivalent to pistil's length or slightly smaller, when considered without the ovary.

*Stamen.*—Size compared to petals — The size of stamen is smaller than the size of petals.

*Color.*—White (RHS WHITE NN155 C).

Anthers:

*Length.*—Small. Approximately 0.5 millimeters.

*Diameter.*—Approximately 0.5 millimeters.

*Form.*—Cordiform (heart-shaped).

*Color.*—Yellow color (RHS YELLOW 12 A). The color evolves with flowering.

*Pollen production.*—Pollen is abundant and has a yellow color (RHS YELLOW 12 A). The fertility has been checked and the 'SWILAM' variety is self-sterile.

Pistil:

*Number.*—Usually 1.

*Length.*—Approximately from 15.0 to 16.0 millimeters including the ovary, that is equal or higher than stamens length.

*Position pistil in comparison to stamens.*—Pistils are above or at the same level as stamens.

*Color.*—Considered pale green (RHS YELLOW GREEN 150 C).

*Surface texture.*—Smooth and glabrous.

*Pubescence.*—Absent.

*Stigma.*—Approximately 1.0 millimeter in diameter, with a round shape and a greenish color (RHS YELLOW GREEN 151 A or RHS YELLOW GREEN 152 D).

*Ovary.*—Approximately 2.0 to 3.0 millimeters in height. The diameter of the ovary is about 1.5 to 2.0 millimeters. The color is considered dark green (RHS YELLOW GREEN 143 B).

Type of reproduction: Pollination by another cherry variety flowering at the same time.

Pollinator: The following varieties are good pollenizers of 'SWILAM': 'SWEETHEART' cherry tree (non patented), 'BIGALISE' cherry tree (non patented), 'BICOLAM' cherry tree (U.S. Plant Pat. No. 31,686), 'FIRELAM' cherry tree (U.S. Plant Pat. No. 25,564), 'RAINIER' cherry tree (non patented).

Fruits:

*Maturity when described.*—Firm at maturity.

*Date of first picking.*—The first picking begun on May 28, 2021. The date of picking varies slightly with climatic conditions.

*Date of last picking.*—Last known picking times carry on from May 28$^{th}$ to Jun. 4, 2021, then from June 8$^{th}$ to Jun. 15, 2022, then from May 26$^{th}$ to Jun. 2, 2023, then from June 3$^{rd}$ to Jun. 10, 2024, and then from June 4$^{th}$, to Jun. 11, 2025.

*Ripening period.*—The 'SWILAM' variety is considered to show a medium maturity period. The maturity period is grouped within approximately 7 to 8 days.

Figure 3:
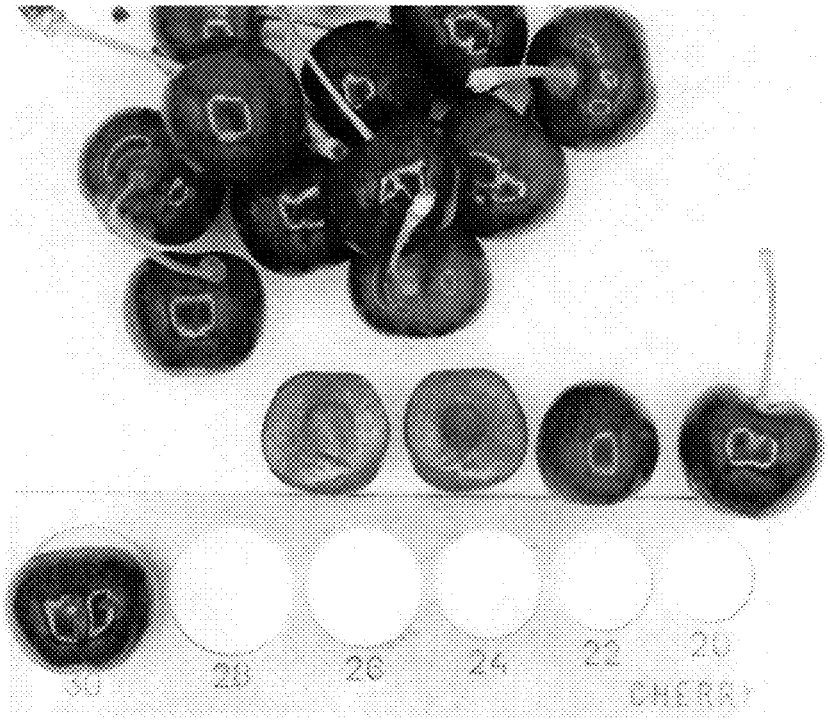
FIG. 3 is a color photograph which shows whole fruits of the new variety, and one fruit having been cut in half, with the stone being left in one of the halves, for depicting the fruit flesh, the stone, and the stone cavity of the new variety, a typical cherry size scale is also shown in the photograph to illustrate the size of the fruit of the new variety.
Figure 4:
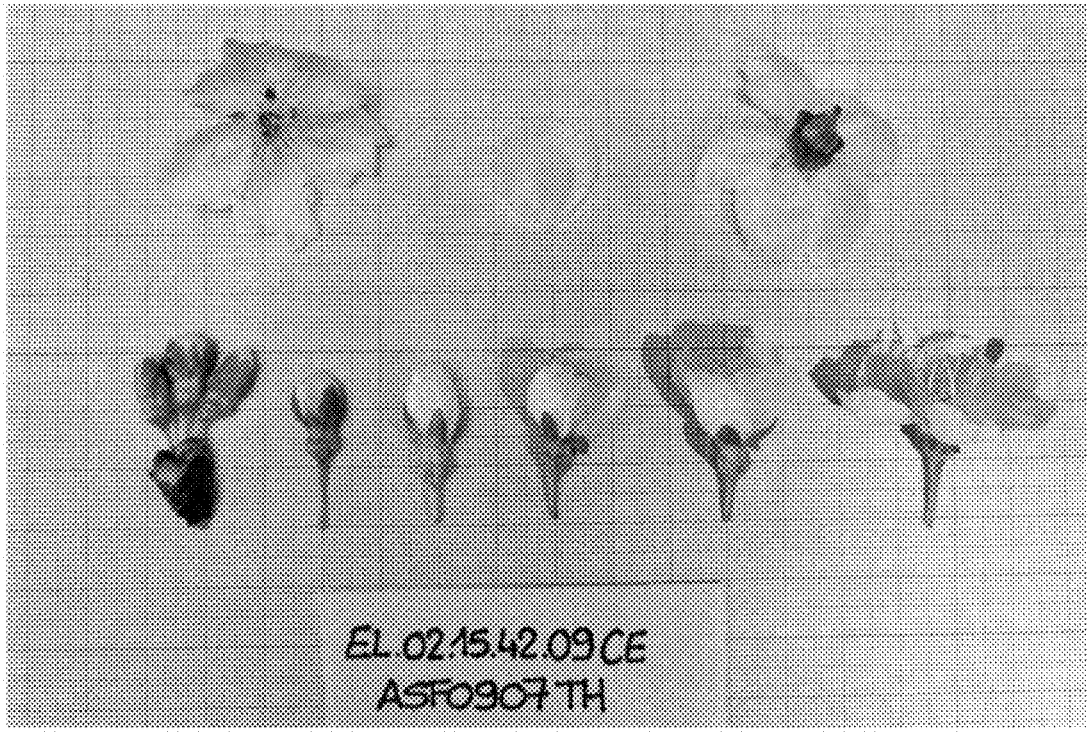
FIG. 4 is a color photograph which shows typical white flowers of 'SWILAM' variety at blooming for depicting the flower buds at different stages of development; and the reverse and side view of the flowers and the reproductive organs with petals removed, of the new variety, also named 'EL.02.15.42.09CE' or 'ASF0907TH' as set forth above.
Figure 5:
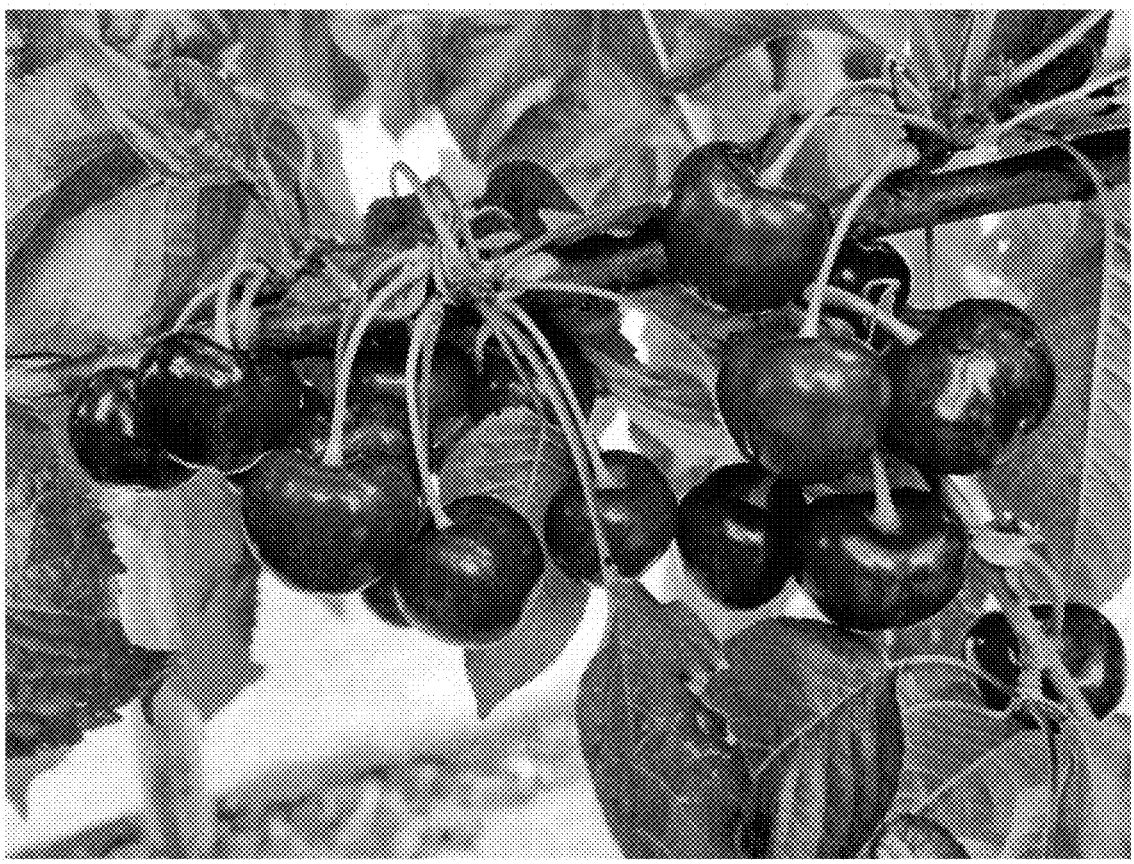
FIG. 5 is color photographs that shows a close view of typical fruits of the new variety 'SWILAM' at ripening time, on a branch of a tree, in orchard.
Figure 6:
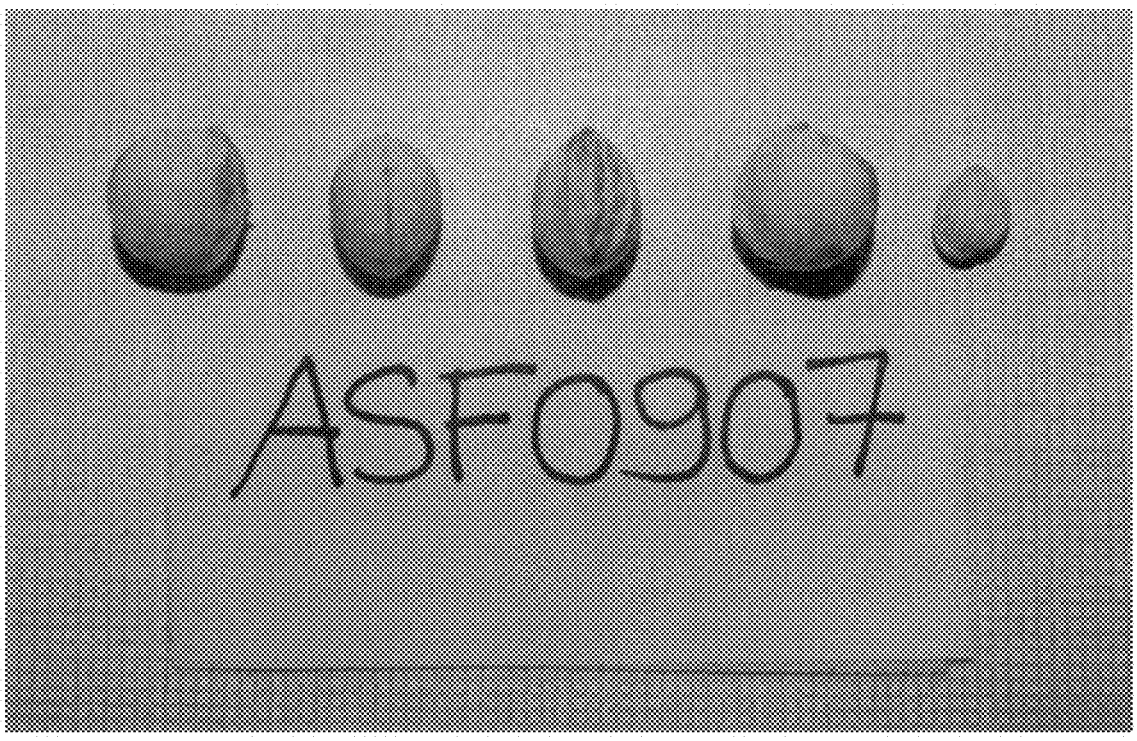
FIG. 6 is a color photograph showing different views of the stone of the new variety also named 'ASF0907' as set forth above and the kernel of the stone.

Size:

*Generally*.—Considered large, with a homogeneous size between them. The size of the fruits ranges from 30 to 32, as illustrated on FIG. 3, that shows a fruit with a size 30.

*Average cheek diameter*.—About 23.0 to 25.0 millimeters.

*Average axial diameter*.—About 22.0 to 24.0 millimeters.

*Typical weight*.—Considered big. Generally about 7.0 grams. This characteristic is highly dependent upon the prevailing cultural practices, and therefore is not particularly distinctive of the variety.

Fruit form:

*Generally*.—Reniform and regular.

*Fruit suture*.—Absent.

Ventral surface:

*Form*.—Smooth.

*Apex*.—Round. Slightly in depression.

*Base*.—Slightly in depression.

*Stem cavity*.—Average depth of the stem cavity is about 1.0 to 2.0 millimeters. The stem cavity is shallow. Average width is about 8.0 to 10.0 millimeters, with a flared shape.

*Mucron*.—Absent.

Fruit skin:

*Thickness*.—Considered thin, and tenacious to the flesh depending on stage of maturity.

*Tenacity*.—Tenacious to flesh and strong.

*Texture*.—Smooth and glabrous.

*Taste*.—Semi-sweet.

*Tendency to crack*.—None.

*Lenticels*.—Absent.

Color:

*Blush color*.—The color of the fruit is considered dark red. When the fruits are mature, the fruit skin is colored over its entire surface with a homogenous dark red (RHS GREYED PURPLE N186 B to RHS GREYED PURPLE N186 C).

*Fruit stem*.—Considered medium to long, approximately 23.0 to 27.0 millimeters.

*Diameter*.—Approximately 1.0 millimeters.

*Color*.—Light green (RHS YELLOW GREEN 144 B).

*Description*.—Resistant and flexible, no splitting when removed.

Flesh:

*Ripens*.—Homogenous and regular. The fruit can be eaten as soon as it is harvested.

*Texture*.—Very crunchy, dense.

*Fibers*.—No fibers.

*Firmness*.—Considered firm. The firmness of 'SWILAM' fruits is between 65 and 74 on the Duforel scale.

*Aroma*.—Good presence.

*Eating quality*.—Good to very good, semi-sweet, aromatic.

*Flavor*.—Semi-sweet, sugary, aromatic. Slightly acid.

*Juice*.—Large amount, very juicy.

*Brix*.—Approximately 17.1 to 20.0 degrees, with a medium degrees Brix of 18.8. This characteristic varies slightly with amount of fruit per tree and climatic conditions.

*Color of juice*.—The juice has a red color (RHS RED 46 A) at ripeness.

*Color of flesh*.—Dark red or blood red (RHS RED 187 A), and the color of flesh in the stone cavity and around the stone cavity is similar.

Stone:

*Type*.—Freestone at fruits picking.

*Size*.—Small for the variety.

*Length*.—Approximately 10.0 millimeters.

*Width*.—Approximately 9.0 millimeters.

*Diameter*.—Approximately 7.0 millimeters.

*Form*.—Round.

*Base*.—Generally round.

*Apex*.—The apex is not marked.

*Stone cavity*.—Small with a form and dimensions corresponding to the stone's dimensions.

Stone surface:

*Surface texture*.—Smooth.

*Ridges*.—None, smooth.

*Tendency to split*.—Splitting is absent.

Ventral edge:

*Width*.—Very shallow, more or less 0.5 millimeter.

Dorsal edge:

*Shape*.—Fully, without any relief.

Stone color: The color of the dry stone is light beige (RHS GREYED YELLOW 161 C).

Kernel:

*Size*.—Small.

*Length*.—About 4.0 millimeters.

*Width*.—About 3.0 millimeters.

*Thickness*.—About 3.0 millimeters.

*Form*.—Round.

*Pellicle*.—Not pubescent, smooth.

*Color*.—The kernel skin is beige (RHS ORANGE WHITE 159 D). The kernel and its embryo (almond) are mature at the time of fruit maturity.

*Almond*.—The almond has a sweet taste and a beige color (RHS ORANGE WHITE 159 D), similar to the color of the skin of the kernel.

Use: Dessert. Fresh products.

*Market*.—Local and long distance. On the tree fruits can stay 10 days while keeping good gustative qualities. The lifetime after picking is also good.

Keeping quality: Good, held well for 30 days in cold storage at 2° C. and maintained good appearance and eating quality.

Shipping quality: Good, showed minimal bruising or scarring during picking, packing and shipping trials.

Plant/fruit disease resistance/susceptibility: Specific tests were run and 'SWILAM' variety seems to be low sensitive to other observed pathologies, to cracking and to conservation pathologies.

The present new variety of cherry tree, its flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

I claim:

1. A new and distinct variety of cherry tree named 'SWILAM', substantially as illustrated and described, characterized by its medium ripening period, its fruits and especially by its large size, its dark red colored fruit skin, its firmness, good flavor and eating quality; the fruit is further characterized by its good handling and storage qualities.

* * * * *